United States Patent
Kawaguchi

(12) 
(10) Patent No.: US 6,663,791 B1
(45) Date of Patent: Dec. 16, 2003

(54) DETECTION METHOD OF COATING FILM THICKNESS AND ION IMPLANTATION EQUIPMENT USING THIS METHOD

(75) Inventor: Hiroshi Kawaguchi, Toyo (JP)

(73) Assignee: Sumitomo Eaton Nova Corporation (JP)

( * ) Notice: Subject to any disclaimer, the term of this patent is extended or adjusted under 35 U.S.C. 154(b) by 24 days.

(21) Appl. No.: 09/632,039

(22) Filed: Aug. 3, 2000

(30) Foreign Application Priority Data

Aug. 5, 1999 (JP) .......................................... 11-222636

(51) Int. Cl.[7] ........................ G01R 29/00; G01R 17/02; G01R 19/10; G01D 3/08; G01N 27/00
(52) U.S. Cl. ............................. 216/61; 427/10; 73/86; 73/865.9; 73/866.2
(58) Field of Search ....................... 427/10, 9; 216/61; 73/86, 865.9, 866, 866.2, 432.1; 315/111.81

(56) References Cited

U.S. PATENT DOCUMENTS

| | | | | |
|---|---|---|---|---|
| 4,085,022 A | * | 4/1978 | Wechsung et al. | 204/298 |
| 4,962,461 A | * | 10/1990 | Meyer et al. | 427/10 |
| 5,134,301 A | * | 7/1992 | Kamata et al. | 250/492.2 |
| 5,396,076 A | * | 3/1995 | Kimura | 250/492.21 |
| 5,947,053 A | * | 9/1999 | Burnham et al. | 116/208 |
| 5,948,217 A | * | 9/1999 | Winer et al. | 204/192.34 |

* cited by examiner

*Primary Examiner*—Marianne Padgett
(74) *Attorney, Agent, or Firm*—Watts Hoffmann

(57) ABSTRACT

A detection method of coating film thickness and an ion implantation equipment using the detection method. The detection method comprises providing on a surface of materials, such as disk (11) of a wafer support on which a coating film comprising a low conductive material, an electrical measurement sensor (18) having a coating film comprising the same material, and detecting thickness change of the coating film on the surface of the materials by irradiation with particle beams in the form of a signal from the sensor (18). The ion implantation equipment comprises an electrical measurement sensor provided on a disk and having a sample piece that forms a coating film of the same material as that of a surface coating of the disk, and means to monitor thickness change of the coating film by sensor signal from the measurement sensor.

6 Claims, 4 Drawing Sheets

DETECTION METHOD OF COATING FILM THICKNESS AND ION IMPLANTATION EQUIPMENT USING THIS METHOD

FIELD OF THE INVENTION

The present invention relates to a detection of a state of a coating film thickness on a surface of equipment and an object, such as a disk, used in ion implantation and the like. The present invention further relates to a method for detecting a state that a coating film on disk surface wears thin or a fact that potion at which the coating film has worn off. The present invention also relates to a monitoring of a thickness of a coating film on a disk surface.

BACKGROUND OF THE INVENTION

In an ion implantation equipment, heretofore, an aluminum alloy having lightweight, excellent strength and good heat conductivity has used as a material for a disk 1 having a wafer 2 mounted thereon as shown in FIG. 1. However, in the case where the disk is produced with an aluminum alloy, there is the possibility that an alloy composition material including aluminum is sputtered with ion beams to contaminate a wafer. For thie reason, a method is employed in which a disk produced by an aluminum alloy is coated with a material such as silicon (Si) to reduce metal contamination from the disk.

However, a coating film on disk surface is gradually weared by sputtering with ion beam irradiation. When the wear reaches an aluminum alloy surface on the disk surface, metal contamination may generate. Therefore, in using a disk having a coating such as silicon on the surface thereof, it is necessary to detect a fact that a coating film on disk surface wears thin or wearing out, and to take a necessary action such as exchange of coating part, before the wear of the coating film reaches a limit.

Coating life could heretofore be predicted from a sputtering rate of coating material with implanted ion. However, implantation conditions (implanted ion species, energy, and implanted dose) vary depending on every ion implantation equipment, so that a life cannot be detected with good reliability with the conventional method. Further, a method of measuring a coating film thickness using a film thickness gauge or the like has a disadvantage that it takes much time for measurement.

A method of indirectly detecting a degree of wear of coating film thickness is not known in the conventional technique. However, according to Japanese Utility Model No. 2,573,028 by the present applicant, an ion implantation equipment was developed in which a table portion supporting a target material is provided on a disk mounting a wafer and the target material is fixed to the table portion, thereby reducing a charge amount of the target material loaded on the table portion with ion implantation.

This device can suppress charge-up with good efficiency by coating a plate of disk (disk cover) mounting a wafer with an appropriate material such as Si or SiC, and also can reduce contamination of a wafer or the like. Further, this device has a countermeasure that a potion to be coated is made small segments, so that coating can be conducted easily.

SUMMARY OF THE INVENTION

The present invention has been made in view of the above circumstances.

One object of the present invention is to provide a detection method of coating film that quickly detects a life of a coating film irradiated with ion beams to prevent a metal substance by sputtering from a surface and having a coating film formed thereon.

Another object of the present invention is to provide an ion implantation equipment using the detection method.

In order to achieve the above objects, the present invention has the following embodiments.

A first aspect of the present invention relates to a detection method of a coating film thickness, which comprises providing an electrical measurement sensor having a coating film comprising a low conductive material on a surface of an object having the same coating film formed thereon, and detecting a thickness change of the coating film on the surface of the object by referring to a value of the signal from the sensor when a particle beam irradiates the surface of the sensor and the object.

According to the above structure, because the electrical measurement sensor and the object are coated with the film of the same material, film thickness change on the surface of the object can be detected through a signal from the sensor obtained by film thickness change of the coating film of the electrical measurement sensor.

A second aspect of the present invention relates to a detection method of a coating film, which comprises the steps of providing an electrical measurement sensor on the surface of a disk which includes a sample piece covered with a coating film comprising the same material formed on a surface of the disk, detecting a change of electrical signals from the sensor when an ion beam irradiates the sample piece during ion implantation, and converting the voltages of the sensor signals to the amount of decrease of the coating film thickness of the disk surface.

According to the above structure, the sample piece of the electrical measurement sensor wears thin with wear of the coating film in the same rate as in the disk, and the degree of wear of the coating film on the disk surface can be detected from a sensor signal from the sample piece.

According to the second aspect of the present invention, the method comprises detecting, as a change of sensor signal, a change of a charge amount due to flowing a material having electric charge into the sample piece of the electrical measurement sensor, and measuring the change of film thickness of the coating material based on this change detecting a change of electrical signals from the sensor when an ion beam irradiates the sample piece during ion implantation, and converting the voltages of the sensor signals to the degree of decrease of the coating film thickness of the disk surface.

According to the above structure, the change of film thickness of the coat film of the sample piece is approximately proportional to the change of the charge amount by charged particles of ions or electrons by ion beams flowing into the sample piece, so that this makes it possible to detect the degree of wear of the coating film on the disk surface from the charge amount of the sample piece.

According to the second aspect of the present invention, the method comprises further step of providing a reference sensor placed on the disk apart from the wafer, which consists of the same material as the disk and has the same area exposed to ion the beam as the sensor but has no coating film, and detecting a time when the sensor signal by electrical measurement sensor having the coating film consists with the reference value of a sensor signal obtained from the reference value sensor.

According to the above structure, the signal from the reference sensor with no coating material of the same material as the disk can be compared with the sensor signal from the electrical measurement sensor at the time when the coating film of the electrical measurement sensor wears and the surface of the same material as the disk is exposed, and when two sensor signals are of equal value, it is possible to detect that the coating film thickness on the disk surface has worn out.

A third aspect of the present invention relates to an ion implantation equipment comprising an electrical measurement sensor provided on a disk and having a sample piece covered with a coating film of the same material as that of a surface coating of the disk, and means to monitor thickness change of the coating film by sensor signal from the measurement sensor.

According to the above structure, the wear state of the coating film of the disk is detected as sensor signal from the sample piece of the electrical measurement sensor.

According to the third aspect of the present invention, the degree of wear of the coating film thickness of the electrical measurement sensor can be determined by a control unit.

According to the third aspect of the present invention, ion beams are scanned uniformly and around disk periphery relative to the wafer surface by the rotational and reciprocal movement of the disk. Therefore, if at least one electrical measurement sensor is arranged between wafers, the same thickness change of the coating film as that of the disk surface is obtained in the range of beam irradiation region.

According to the third aspect of the present invention, the coating film thickness of the sample piece is the same or slightly smaller than that of the disk. As a result, the remaining thickness of the coating film of the sample piece can be the same as or slightly smaller than that of the disk surface.

According to the third aspect of the present invention, film thickness change of the electrical measurement sensor is detected as the change of the sensor signal voltage generated relative to ground potential. Therefore, change of the coating film can easily be detected by measuring equipment such as a voltage indicator.

According to the third aspect of the present invention, because the coating face of the electrical measurement sensor is arranged at a position higher or lower than that of the disk, the sample piece of the sensor does not receive influence of sputtering from the disk face. Further, if the disk and each coating film of the sensor are arranged at the same plane, the irradiation conditions of ion beams are the same. As a result, the coating film thickness varies in the same proportion, and detection accuracy can further be improved.

According to the third aspect of the present invention, because the coating face of the electrical measurement sensor is arranged at a position higher or lower than the position of the disk, the sample piece of the sensor does not receive influence of sputtering from the disk face. Further, if the disk and each coating film of the sensor are arranged at the same plane, the irradiation conditions of ion beams are the same. As a result, the coating film thickness varies in the same proportion, and detection accuracy can further be improved.

According to the third aspect of the present invention, because the reference sensor having a small detection face of the same material as in the disk face not coated with coating film, thickness change of the coating film can be detected by comparing each sensor signal of the electrical measurement sensor and the reference sensor.

BRIEF DESCRIPTION OF THE DRAWINGS

FIGS. 3($b$), 3($c$) and 3($d$) each are views showing other practical embodiments of fixing structure of the electrical measurement sensor shown in FIG. 3($a$).

DETAILED DESCRIPTION OF THE INVENTION

The embodiments of the present invention are explained below based on the accompanying drawings.

Figure 4:
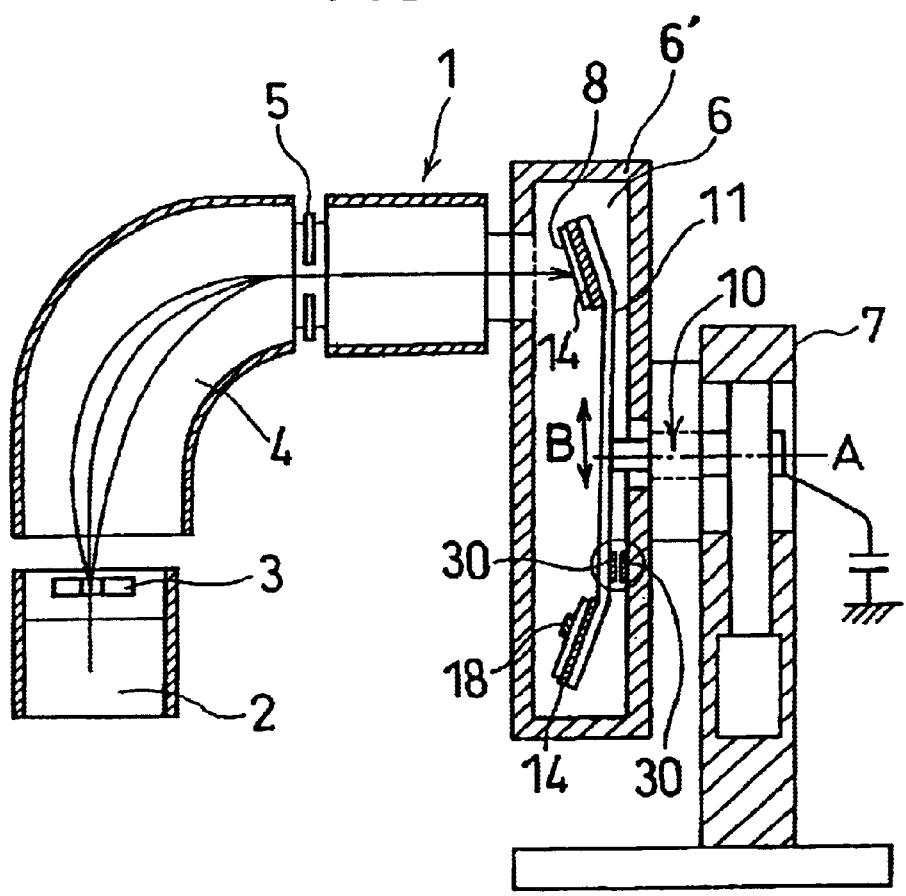
FIG. 4 is a schematic structural view of an ion implantation equipment used in the present invention.

FIG. 4 shows general ion implantation equipment 1 having the following structure. The ion implantation equipment 1 is equipped with an ion source 2, an extraction electrode 3, a mass analyzer 4, a mass analyzing slit 5 and a disk chamber 6 for wafer analyzing. A wafer support 10 for mounting a wafer 8 is arranged in the disk chamber 6 supported by a base table 7. This wafer support 10 has a disk 11 in its front. The disk is rotationally driven with a center of a rotating axis A and also can reciprocally move in a direction B vertical to the rotating axis. Ion beams scan on the wafer.

Materials used for mounting a wafer in ion implantation of the disk 11 in general is constituted of a metal such as aluminum, and a pedestal 14 for mounting a plurality of wafer, that removably fixes the wafer 8, is provided on the disk. Further, the entire surface or part of the surface of disk excluding the face of the pedestal 14 is coated with a coating material such as silicon.

The coating film 16 (shown in FIG. 1) is a substance generally called a low conductive substance, i.e., a substance having an electric conductivity smaller than that of the disk material (such as aluminum) and limitatively a substance showing an electric conductive value near zero without limit. This substance includes semi-conductor substances such as silicon (Si, SiC) or the like.

In the present practical embodiment, the coating film is formed on the disk itself. However, it is sufficient if only the surface coating covers the surface of the disk to be irradiated with particle beams or ion beams. Therefore, the coating may be formed on the surface of a disk cover that is divided and fixed onto the disk surface with bolts or the like. In this case, a phenomenon that metal molecules are released from the disk surface by sputtering due to ion implantation and adhered on the wafer is prevented so long as the coating film on the disk surface does not wear out.

Figure 1:
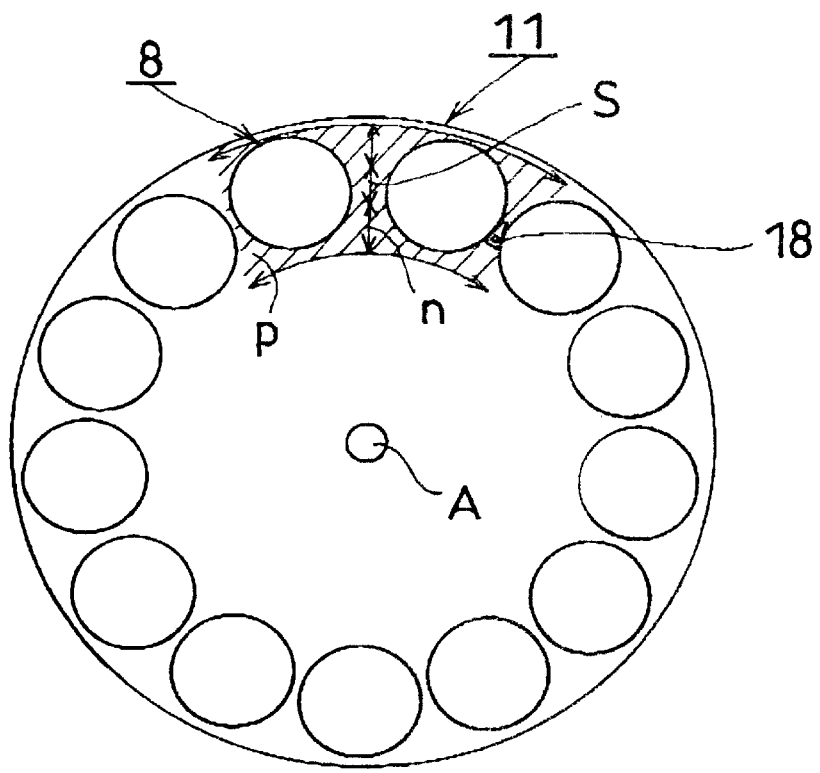
FIG. 1 is a plane view in which one electrical measurement sensor is provided on a disk mounting a wafer according to the present invention.

As shown in FIG. 1, at least one electrical measurement sensor 18 is arranged in a region in the disk chamber 6 that is irradiated with ion beams, that is, in the position away from the wafer on the disk. This electrical measurement sensor 18 is constructed so as to be electrically insulated from disk 11 and detect the coating film thickness of the disk surface by means of a sensor signal.

As shown in FIG. 1, preferably, at least one electrical measurement sensor 18 is arranged between pedestals 14 for mounting wafer, arranged on the periphery of the disk. The fixing position of the measurement sensor is theoretically in a range (an area partially shown by an oblique line in FIG. 1) of a circular region having a length of irradiation width of ion beam in a radius direction of disk (S) plus 2 times of radius direction moving distance by reciprocal movement of disk (n), i.e., in P region, and this is an area excluding the region on which wafer is arranged.

Figure 2:
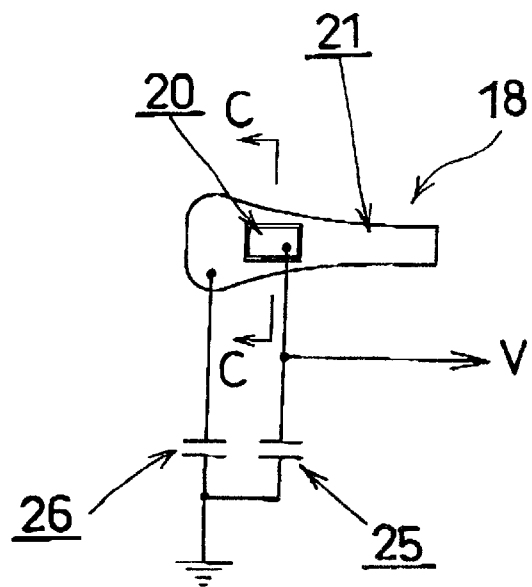
FIG. 2 is a view showing the structure of an electrical measurement sensor according to the present invention.
Figure 3:
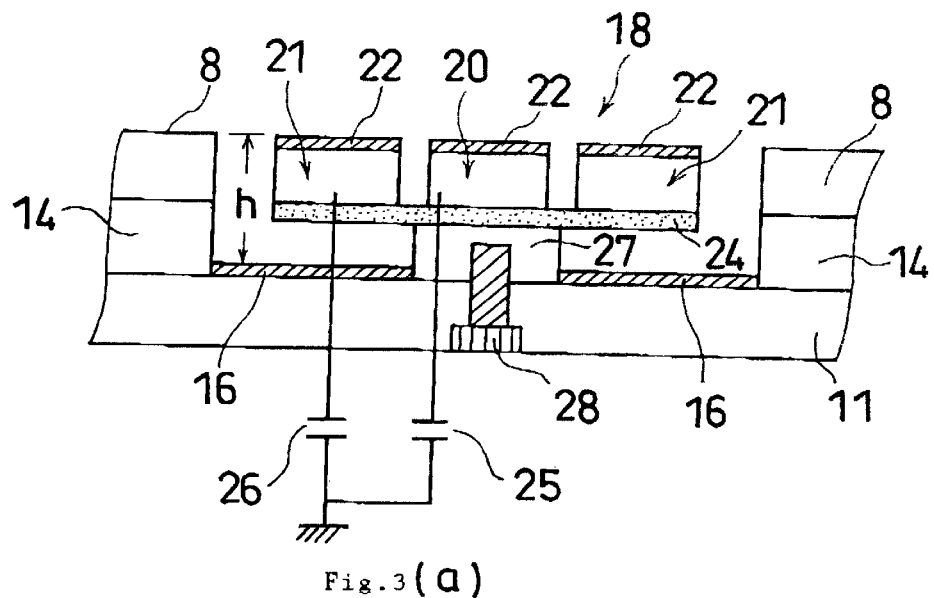
FIG. 3($a$) is a view showing a sectional structure on the disk of the electrical measurement sensor shown in FIG. 2 taken along line C—C.
Figure 3:
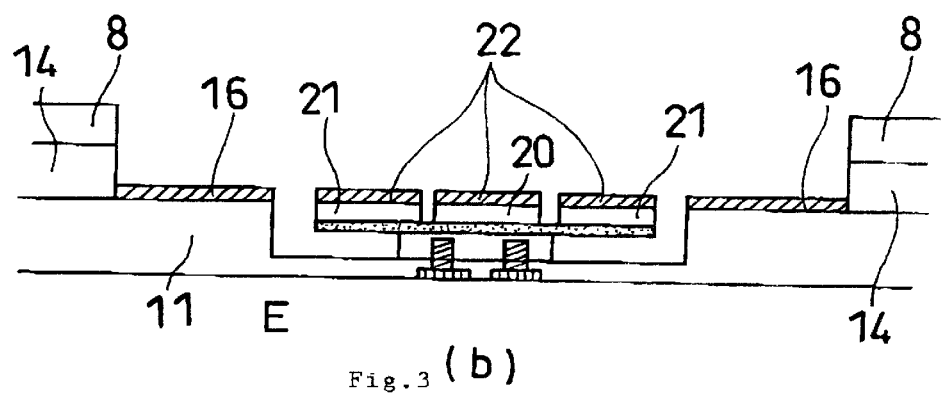
Figure 3:
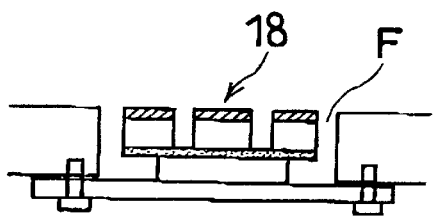
Figure 3:
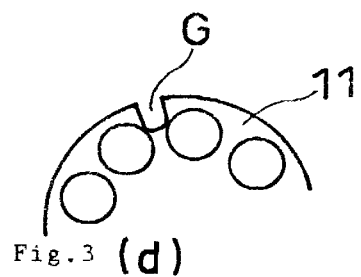

FIG. 2 and FIG. 3(a) show one practical embodiment of the electrical measurement sensor 18 according to the present invention. The electrical measurement sensor 18 is arranged between wafers 8, 8, and has two electrodes comprising a sample piece 20 comprising small sensor chip and a plate 21 covering around the chip, a coating film 22 of a material such as silicon or the like applied to the surface of those electrodes, and an insulator (insulating part) 24 that separates each electrode from the disk 11.

Each electrode of the sample piece 20 and the plate 21 is generally made of aluminum, and has a sandwich structure such that the upper side of the electrode is covered with the coating film 22 of silicon similar to the disk portion, and the insulator 24 is arranged at the lower side thereof. Each of those electrodes is insulated from the disk 11 by the insulator 24, and connected to one condenser 25 or 26 through an electric wire, and other edge of each condenser is ground to an earth terminal. The sensor 18 is fixed to the disk such that the sensor support 27 arranged at the bottom side of the insulator 24 is fixed from the back of the disk using a fixture such as a screw 28.

The electrical measurement sensor 18 can detect with only the sample piece 20. However, it is preferable to constitute such that the periphery of the sample piece 20 is surrounded by the plate 21 for disturbance noise prevention ground through another condenser 26, as shown in FIG. 3(a). The sensor 18 is constituted such that the ground voltage and the voltage between condensers 25 connected between the samples 20 are output as a sensor signal V.

The electrical measurement sensor 18 thus constituted may be arranged at any position on the disk surface, excluding the wafer mounting region, if receiving irradiation with beams. The upper surface of the wafer 12 mounted and fixed on the pedestal 14 and the detecting surface of the electrical measurement sensor 18 are arranged at an appropriate height on the upper surface of the disk. However, it may be constituted such that those have approximately the same height h from the upper surface of the disk as shown in FIG. 3(a).

Contrary to FIG. 3(a), a depression space E is formed in the disk (see FIG. 3(b)) or a through-hole F is formed in the disk (see FIG. 3(c)) or a notch G is formed at the edge of the disk (see FIG. 3(d)), and the electrical measurement sensor 18 can be provided therein. The electrical measurement sensor 18 is fixed to the disk such that the support 23 at the bottom side of the insulator 24 is fixed with a screw from the back of the disk.

Intensity of signal of the electrical measurement sensor varies depending on the conditions of ion implantation. For example, in the case that the coating film on the surface of the sample piece 20 does not wear off, the intensity of signal is about 10 V, and in the case that the coating film has worn out, the intensity of signal is about 30 V. Therefore, by the voltage change between those, it is possible to detect the degree of wear of the coating film.

As explained above, the electrical measurement sensor according to the present invention is arranged with a certain distance from the disk such that the coating face has a position higher or lower than the disk face, and a plate surrounding around the sample piece is arranged. Therefore, the sample piece of the sensor does not receive the influence of sputtering from the disk face. Further, when each coating film of the disk and the sensor is arranged on the same plane, irradiation conditions of ion beams are the same. As a result, the coating film thicknesses change at the same proportion, and it is possible to further improve detection accuracy.

Detection method of the coating film thickness of the present invention and actuation of the sensor are explained using the electrical measurement sensor 18 shown in FIG. 2.

First, the electrical measurement sensor having a sample piece forming a coating film of the same material as that of a coating on the disk surface is fixed on a disk provided in a disk chamber of an ion implantation equipment.

When ions or electrons collide with a sensor chip 20 that is a sample piece during ion implantation, voltage V generates relative to ground potential. This voltage is picked up from a rotating disk 11 by a direct wiring or by electrostatic coupling due to an electrostatic coupling element 30 provided as a pair in the back of the disk 11 and the disk chamber, and transmitted to the base table 7 side. Change of charge amount in the sample piece of the electrical measurement sensor, i.e., voltage change, is output as a sensor signal.

Figure 5:
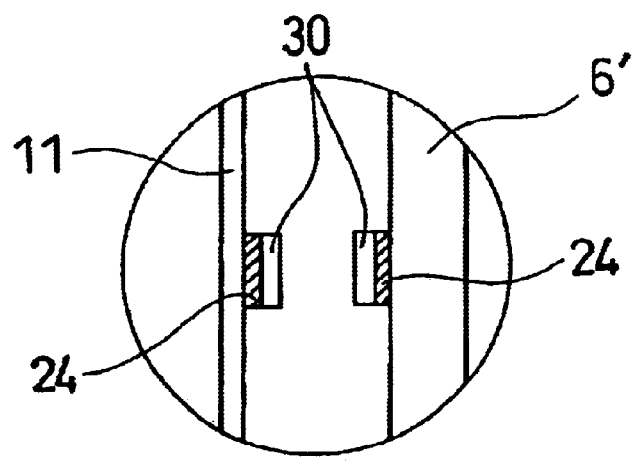
FIG. 5 is an enlarged view showing the arrangement of an electrostatic coupling element, which is a part of the structure in FIG. 4.

FIG. 5 is an enlarged view of a section of FIG. 4, showing a portion of an electrostatic coupling. As illustrated, a wall structure 6' forms the disk chamber interior 6, as best shown in FIG. 4. On opposing interior faces of the wall structure 6' and the disk 11, a pair of opposing electrostatic elements 30 are shown insulated from the wall structure 6' and the disk 11 by an insulator 24.

Film thickness (generally several hundreds μm) of the coated surface on the sample piece 20 of the electrical measurement sensor 18 used in the present invention is nearly the same as that of the disk portion. However, if the coating film thickness of the sensor is slightly thinner than that of the disk portion so that the coating film wears earliest on the disk surface, detection period that the coating film has worn out can slightly be quickened, and the exchange period of the disk can appropriately be determined based on this detection.

According to another practical embodiment of the present invention, the reference value sensor having small detection face and having no coating film of the same material as that of the disk material is provided on the disk at a position apart from the wafer, and the coating film thickness is detected by the electrical measurement sensor and the reference value sensor. That is, the fact that the coating film on the disk face has worn out can be confirmed by detecting the time at which sensor signal by the electrical measurement sensor having a coating film consists with the reference value of sensor signal obtained by the reference value sensor.

Figure 6:
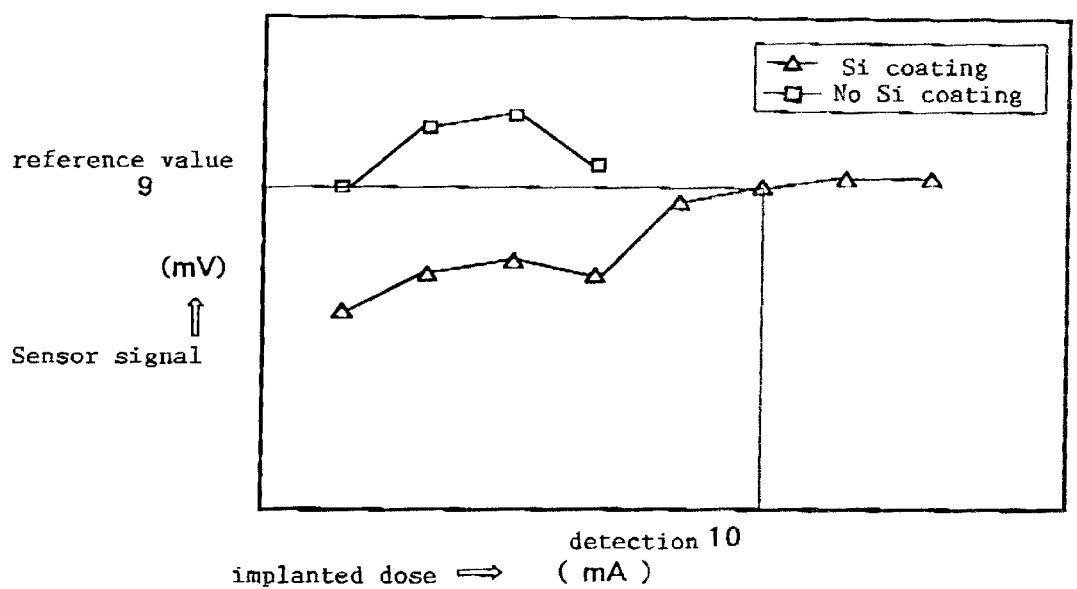
FIG. 6 is a graph showing the relationship between sensor signal and implantation dose according to the present invention.

FIG. 6 shows the measurement results of sensor signal regarding a disk coated with silicon in the above embodiment. This graph shows signal in the case that silicon coating is conducted on sensor chip surface and signal in the case that silicon coating is not conducted to the sensor chip. Sensor signal shows small value in the state that silicon coating on the sensor chip surface does not wear. On the other hand, if implanted dose increase, thereby proceeding sputtering and the wear proceeds until that aluminum exposes on a part of the surface of the sensor chip 20, the sensor signal is the same degree of intensity in the case that silicon coating is not conducted.

Detection of life of the coating film by this sensor is conducted as follows. Intensity of sensor signal in the state that coating such as silicon is not applied to the sensor chip surface is used as a reference. Electrical measurement sensor having the same structure as in the reference value having small size and made of the same material as the disk surface not coated is arranged on the disk. Prior to or during ion implantation, the sensor signal value may be appropriately referred as a reference value or a correction value.

It is detected that the silicon coating wears and approaches its life at the time when the sensor signal equals to the reference value by appropriately comparing the sensor signal with the reference value during ion implantation using the silicon coated disk.

When it is constituted such that the coating film thickness of the electrical measurement sensor chip is slightly thinner than that of the disk portion, the silicon coating of the sensor chip wears out earliest on the disk surface. As a result, at the time when the silicon coating on the sensor chip has worn out, the coating on other disk portion slightly remains. Since area of the sensor chip is small, even if the coating on the surface thereof has worn out, it does not result in increasing metal contamination. By those actions, the life can be detected with good accuracy before the silicon coating on the disk surface wears out.

Pedestal for mounting each wafer on the disk and electrical measurement sensor are arranged on the disk. Upper face of the wafer mounted and fixed and detection face of the electrical measurement sensor may have different location height relative to the disk upper face, and there is no problem on detection with the electrical measurement sensor. However, if the electrical measurement sensor is arranged slightly projecting on the disk so that the upper face of the wafer mounted and fixed and the detection face of the electrical measurement sensor have approximately the same height from the disk upper face, the conditions become the same conditions and detection accuracy improved.

According to further practical embodiment of the present invention, it can be constituted such that change of film thickness of the coating film is detected as change of sensor signal from the change of charge amount due to flowing a substance having electric charges into a sensor.

Change of charge amount of the sample piece can be detected as voltage change between condensers. Further, change causes in sensor signal output from this voltage change, and coating film thickness is calculated using a reference table previously measured.

In order to detect the degree of wear of the coating film on the disk surface based on the value of sensor signal, the relationship between coating film thickness on the sensor and intensity of sensor signal is previously examined using several sensors having different coating film thicknesses, and this is memorized in a control unit as a reference table. The control unit calculates coating film thickness from intensity of sensor signal at the time of actual ion implantation using the reference table. Lower limit of the coating film thickness (upper limit of the sensor signal) is previously determined, and in the case that the measured value deviates from this value, it may be controlled by providing interlock so as not to conduct implantation operation.

As explained above, according to the method of the present invention, the disk has a coating film thickness detecting function by a sensor.

According to the present invention, electrical measurement sensor having a coating film of the same material as that of a surface coating of materials for mounting wafer is provided on the surface of materials, and change in thickness of this coating film is detected as sensor signal. As a result, life of the film can be detected with good timing before the coating film on the disk surface wears out, and its detection accuracy can be improved. In addition, it is possible to shorten the time required for examination of the degree of wear of the coating film.

Further, according to the present invention, electrical measurement sensor and reference value sensor are provided. As a result, the surface of materials or disk has a coating film thickness detecting function by sensor. Also sensor signal is properly compared with the reference value during ion implantation and at the time when the sensor signal equals to the reference value, it is possible to detect that the coating film on the disk surface wears and approaches its life.

At least one electrical measurement sensor is arranged on a disk at a position apart from a wafer within a range on the disk irradiated with ion beams by rotational or reciprocal movement of the disk. Therefore, coating films on small detection face of a sample piece of a sensor and a disk face wear with the same rate. As a result, change of charge amount flowing into a sample piece is monitored as sensor signal, and this makes it possible to detect film thickness change of the coating film on the disk surface.

Further, by making the constitution such that coating film thickness of a sample piece of electrical measurement sensor is slightly smaller than that of disk portion, so that it is possible to avoid a direct exposure of the metal material of disk by wearing of coating film on the disk surface. As a result, disadvantage such as sputtering on the exposed metal surface of the disk material can previously be prevented and a disk can be exchanged at an appropriate period.

Other than the ion implantation equipment, the method according to the present invention can also apply to life detection of silicon coating film in the case that portion coated with silicon or the like is irradiated with ion beams.

What is claimed is:

1. A method for detecting a thickness of coating film, comprising the steps of:
   providing a coating material forming a coating film comprising a low conductive material having a conductivity that is lower than that of aluminum;
   providing a disk having a wafer support device for mounting a wafer thereon, wherein a surface of said disk is coated by said coating material;
   providing an electrical measurement sensor which is fixed on said surface of said disk; said electrical measurement sensor has electrodes covered with said coating film of generally the same material that coats said disk;
   irradiating said wafer, said disk and said sensor with an irradiating beam of ions while said disk is being rotated; and
   outputting an electrical change as a sensor signal when ions from said ion beam strike said sensor to detect a decrease of said coating film thickness on the disk surface during ion beam treatment of said wafer.

2. The method for detecting a thickness of coating film of claim 1, wherein the coating film comprises a low conductive material such as silicon.

3. The method for detecting a thickness of coating film of claim 1 wherein the coating film has a lower conductivity than a material of said disk.

4. The method for detecting thickness of coating film of claim 1, wherein the electrical measurement sensor comprises two electrodes comprising a plate electrode and a sample piece electrode, wherein said sample piece electrode is surrounded with said plate electrode, and wherein said two electrodes are coated by said coating film and insulated from the disk by an insulating portion, and wherein said electrical measurement sensor detects a change of coating film thickness as a change of said sensor signal.

5. The method for detecting a thickness of coating film of claim 4 comprising the steps of:

detecting the change of charge amount due to flow of charged particles into the sample piece electrode of said electrical measurement sensor as the change of the sensor signal; and measuring the change of coating thickness based on the change of said sensor signal.

6. The method for detecting a thickness of coating film of claim 1 further comprising the steps of:

providing a reference value sensor placed on the disk apart from the wafer, wherein said sensor comprises the same material as the disk and has a limited detection face with no coating film; and detecting a time when the value of the sensor signal from said electrical measurement sensor is nearly equal to the value of the sensor signal from the reference value sensor.

* * * * *